(12) United States Patent
Breton

(10) Patent No.: US 6,379,655 B1
(45) Date of Patent: Apr. 30, 2002

(54) PHOTOPROTECTIVE/COSMETIC COMPOSITIONS COMPRISING AMINOAMIDINE SUNSCREENS

(75) Inventor: Philippe Breton, Le Chesnay (FR)

(73) Assignee: Societe l'Oreal S.A., Paris (FR)

( * ) Notice: Subject to any disclaimer, the term of this patent is extended or adjusted under 35 U.S.C. 154(b) by 0 days.

(21) Appl. No.: 09/722,473

(22) Filed: Nov. 28, 2000

(30) Foreign Application Priority Data

Nov. 29, 1999 (FR) .............................. 99 14999

(51) Int. Cl.[7] .......................... A61K 7/42; A61K 7/44; A61K 7/00
(52) U.S. Cl. .................... 424/59; 424/60; 424/400; 424/401
(58) Field of Search .................. 424/59, 60, 400, 424/401

(56) References Cited

U.S. PATENT DOCUMENTS 5,298,647 A  3/1994  Robert et al. ............ 560/16

OTHER PUBLICATIONS

Billington, et al., "Synthesis and Antimycobacterial Activity of Some Heteroarylcarboxamidrazone Derivatives", Drug Design and Discovery, 1993, vol. 3, pp. 269–275.

128: 278800d, "Synthesis and Antihypertensive Activity of Salts of 1–alkylidene(arylidene)benzamidrazones", 6001 Chemical Abstracts, vol. 128, 1998, No. 23.

125632s, "Pyrazine Deviatives", 6001 Chemical Abstracts, vol. 74, 1971, No. 28.

94: 65532K, "Structure Products of the Condensation of Amidrazones with Monocarbonyl Compounds", 6001 Chemical Abstracts, vol. 94, 1981, No. 28.

Chemical Abstracts, Chemical Substance Index, vol. 128, 1998.

*Primary Examiner*—Shelley A. Dodson
(74) *Attorney, Agent, or Firm*—Burns, Doane, Swecker & Mathis, L.L.P.

(57) ABSTRACT

Topically applicable sunscreen/cosmetic compositions well suited for the photoprotection of human skin and/or hair against the damaging effects of UV-irradiation, particularly solar radiation, comprise an effective UV-photoprotecting amount of at least one characteristically novel aminoamidine compound, advantageously having the structural formula (I):

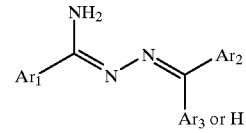

formulated into a topically applicable, cosmetically acceptable vehicle, diluent or carrier therefor.

23 Claims, No Drawings

PHOTOPROTECTIVE/COSMETIC COMPOSITIONS COMPRISING AMINOAMIDINE SUNSCREENS

CROSS-REFERENCE TO PRIORITY APPLICATION

This application claims priority under 35 U.S.C. §119 of FR-99/14999, filed Nov. 29, 1999, hereby expressly incorporated by reference.

BACKGROUND OF THE INVENTION

1. Technical Field of the Invention

The present invention relates to novel cosmetic/dermatological compositions well suited for the photoprotection of the skin and/or of the hair against ultraviolet (UV) radiation, in particular solar radiation, comprising an effective amount of at least one aminoamidine compound.

This invention also relates to the formulation of photoprotective cosmetic/dermatological compositions comprising characteristic aminoamidine sunscreens which are active in the field of UV radiation.

2. Description of the Prior Art

It is known to this art that light radiation having wavelengths of from 280 nm to 400 nm promotes tanning of the human epidermis, and that irradiation having wavelengths more particularly ranging from 280 to 320 nm, i.e., UV-B radiation, causes erythemas and skin burns which can impede the development of natural tanning; this UV-B radiation must therefore be screened from the skin.

It is also known to this art that UV-A radiation having wavelengths of from 320 to 400 nm, which causes tanning of the skin, can also adversely affect it, in particular in the case of a sensitive skin or a skin continuously exposed to solar radiation. UV-A rays cause, in particular, a loss of elasticity of the skin and the appearance of wrinkles, resulting in premature skin aging. Such irradiation promotes the onset of the erythematous reaction or amplifies this reaction in certain individuals and may even be responsible for phototoxic or photoallergic reactions. Thus, for aesthetic and cosmetic reasons such as the preservation of the natural elasticity of the skin for example, an increasing number of individuals wish to control the effect of UV-A rays on their skin. It is therefore desirable to also screen out UV-A radiation.

Numerous compounds for the photoprotection (UV-A and/or UV-B) of human skin are known to this art.

Most are aromatic compounds which absorb UV rays in the region from 280 to 315 nm, or in the region from 315 to 400 nm or else in the entirety of these two regions. These are most often formulated into anti-sun or sunscreen compositions which are provided in the form of an oil-in-water type emulsion (namely, a cosmetically acceptable carrier, vehicle or diluent comprising a continuous aqueous dispersing phase and a discontinuous oily dispersed phase) and which therefore contain, in various concentrations, one or more conventional organic screening agents having an aromatic function, which are lipophilic and/or hydrophilic and which are capable of selectively absorbing harmful UV radiation, these screening agents (and the amounts thereof) being selected according to the desired sun protection factor (the sun protection factor being mathematically expressed by the ratio of the irradiation time necessary to achieve the erythematogenic threshold with the UV-screening agent to the time necessary to achieve the erythematogenic threshold without UV-screening agent).

In addition to their screening power, these compounds exhibiting anti-UV activity should also have good cosmetic properties in the compositions comprised thereof, a good solubility in the customary solvents and in particular fatty substances such as oils and fats, and good stability to UV radiation (photostability).

SUMMARY OF THE INVENTION

It has now surprisingly and unexpectedly been determined that a family of aminoamidine compounds are notable organic UV-screening agents having, in addition to excellent screening properties in the UV-A and/or UV-B radiation regions, a very good solubility in the customary organic solvents and in particular fatty substances such as oils, an excellent photostability, as well as excellent cosmetic properties, rendering same particularly appropriate sunscreens when formulated into cosmetic compositions suited for protecting the skin and/or the hair against the damaging effects of ultraviolet radiation.

DETAILED DESCRIPTION OF BEST MODE AND SPECIFIC/PREFERRED EMBODIMENTS OF THE INVENTION

More particularly according to the present invention, cosmetic compositions for topical application are provided for the photoprotection of the skin and/or of the hair, advantageously comprising, formulated into a cosmetically acceptable carrier, vehicle or diluent therefor, at least one aminoamidine compound having the following structural formula (I):

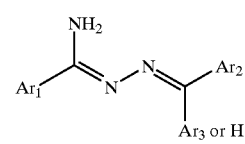

in which $Ar_1$ is (i) an aromatic radical having the following formula (II):

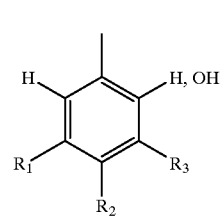

wherein $R_1$, $R_2$ and $R_3$, which may be identical or different, are each a hydrogen atom, a linear or branched $C_1$–$C_8$ alkyl radical, or a $C_1$–$C_8$ alkoxy radical, with the proviso that $R_1$, $R_2$ and $R_3$ can together form an aromatic or unfused ring, or an aromatic heterocycle having 5 or 6 atoms; or (ii) an aromatic radical having 6 atoms, corresponding to the following formula (III):

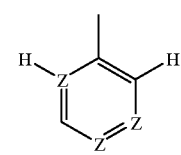

wherein each Z is C or N; $Ar_2$ is an aromatic radical $Ar_1$ as defined above or an aromatic radical having 5 atoms, corresponding to the following formula (IV):

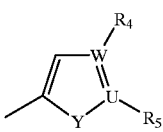

(IV)

wherein Y is a sulfur, oxygen, carbon or nitrogen atom, W is a carbon or nitrogen atom, $R_4$ is (a) a hydrogen atom when W is a nitrogen atom, or (b) a hydrogen atom, a linear or branched $C_1$–$C_8$ alkyl radical, a $C_1$–$C_8$ alkoxy radical, or can form an aromatic or unfused ring member, when W is a carbon atom; U is a carbon or nitrogen atom, when W is a carbon atom; and $R_5$ is (a) a hydrogen atom when U is nitrogen, or (b) a hydrogen atom, a linear or branched $C_1$–$C_8$ alkyl radical, a $C_1$–$C_8$ alkoxy radical, or can form an aromatic or unfused ring member, when U is a carbon atom; and $Ar_3$ is an aromatic radical $Ar_2$ as defined above, or a hydrogen atom.

Various aminoamidine compounds of formula (I) in accordance with the invention are known to this art and a variety thereof are described in the article by BILLINGTON, D. C.; COLEMAN, M. D.; IBIABUO, J.; LAMBERT, P. A.; RATHBONE, D. L.; TIMS, K. J., *Drug Des. Discovery* 15(4), 269–275 (1998).

The aminoamidine compounds of formula (I) according to the invention are conveniently prepared via a three-step synthesis from a nitrile per the following reaction scheme:

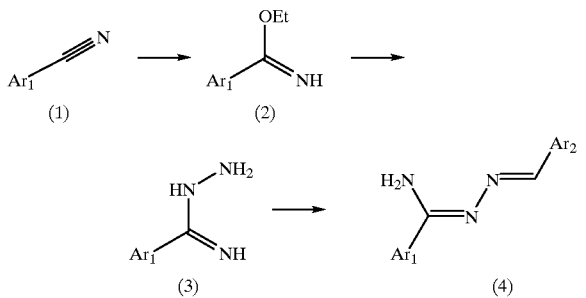

The step which makes it possible to proceed from (1) to (2) is the synthesis of the Pinner iminoethers which is described, for example, in PINNER, A., *Chem. Ber.*, 1877, 10, 1889; ROGER, R. AND NEILSON D., *Chem. Rev.* 1961, 61, 179; RAPOPORT, H., *J. Org. Chem.*, 1981, 46, 2465.

Numerous aromatic nitriles are commercially available, such as, for example:

4-nitrobenzonitrile (cas: 619-72-7) from Acros, reference 12848-0250;

3-cyanopyridine (cas: 100-54-9) from Acros, reference 110861000;

4-aminobenzonitrile (cas: 873-74-5) from Acros, reference 164470100;

4-fluorobenzonitrile (cas: 1194-02-1) from Acros, reference 160810250;

4-acetylbenzonitrile (cas: 1443-80-7) from Acros, reference 167580250.

Certain iminoethers are also commercially available, such as, for example:

ethyl 4-hydroxybenzimidate hydrochloride (cas: 54998-28-6) from Aldrich, reference 32,446-9;

etlylbenzimidate hydrochloride (cas: 5333-86-8) from Fluka, reference 12268.

The step which permits proceeding from (2) to (3) is carried out by the action of hydrazine and is described in the literature, in particular by CASE F. H., *J. Org. Chem.*, 1965, 30, 931 and also TAYLOR E. C. and MARTIN S. F., *J. Org. Chem.*, 1972, 37, 3958, or also by REPIC O., MATTNER P. G. AND SHAPIRO M. J., *J. Heterocyclic Chem.*, 1982, 19, 1201.

The step which permits proceeding from (3) to (4) is the condensation of an aromatic aldehyde in alcoholic medium. This reaction is described in the literature, in particular by MAMOLO M. G.; VIO L.; BANFI E.; PREDOMINATO M.; FABRIS C.; ASARO F., *Farmaco*, 1992, 47, 1055 and also by BILLINGTON D. C.; COLEMAN M. D.; IBIABUO J.; LAMBERT P. A.; RATHBONE D. L.; TIMS K., *J. Drug Des. Dis.*, 1998, 15, 269.

Numerous aromatic aldehydes are also commercially available, such as, for example:

pyrrole-2-carboxaldehyde (cas: 1003-29-8) from Aldrich, reference P7,340-4;

trans-3-(2-furyl)acrolein (cas: 39511-08-5) from Aldrich, reference F2,060-2;

2-methylindole-3-carboxaldehyde (cas 5416-80-8) from Aldrich, reference 26,243-9;

2-furaldehyde (cas: 98-01-1) from Aldrich, reference 31,991-0;

4-methyl-5-imidazolecarboxaldehyde (cas: 68282-53-1) from Aldrich, reference 39,215-4;

1-methylindole-3-carboxaldehyde (cas: 19012-03-4) from Aldrich, reference 35,798-7.

Among the aminoamidine compounds of formula (I) according to the invention, particularly representative are those described in the following Table:

| Compound No. | Formula | Name |
|---|---|---|
| 1 | ![structure] | 5-((E)-{(2Z)-2-amino(phenyl)methylene]-hydrazono}methyl)-2-furansulfonate |

-continued

| Compound No. | Formula | Name |
|---|---|---|
| 2 | | N'-[(E)-1H-imidazol-2-yl-methylidene]benzenecarbohydrazonamide |
| 3 | | N'-[(E)-1H-imidazol-4-yl-methylidene]benzenecarbohyrazonamide |
| 4 | | N'-[(E)-3,3-bisphenyl-2-propylidene]benzenecarbohydrazonamide |
| 5 | | N'-{(E)-[5-(hydroxymethyl)-2-furyl]methylidene}benzenecarbohydrazonamide |
| 6 | | N'-[(E)-(5-chloro-3-methyl-1-phenyl-1H-pyrazol-4-yl)methylidene]benzenecarbohydrazonamide |

| Compound No. | Formula | Name |
|---|---|---|
| 7 | | N'-[(E)-(1-methyl-1H-indol-3-yl)methylidene]benzenecarbohydrazonamide |
| 8 | | N'-[(E)-1H-pyrrol-2-yl-methylidene]benzenecarbohydrazonamide |
| 9 | | N'-[(E)-(2-methyl-1H-indol-3-yl)methylidene]benzenecarbohydrazonamide |
| 10 | | N'-[(E,2E)-3-(4-hydroxy-3,5-dimethoxyphenyl)-2-propenylidene]benzenecarbohydrazonamide |
| 11 | | N'-[(E,2E)-3-(2-furyl)-2-propenylidene]benzenecarbohydrazonamide |

| Compound No. | Formula | Name |
|---|---|---|
| 12 | | N'-[(E)-[2-furylmethylidene]benzene-carbohydrazonamide |
| 13 | | N'-{(E)-[5-(2-chlorophenyl)-2-furyl]-methylidene}benzenecarbohydrazonamide |
| 14 | | N'-{(E)-[5-(4-nitrophenyl)-2-furyl]methylidene}benzenecarbo-hydrazonamide |
| 15 | | N'-[(E)-(4,5-dimethyl-2-furyl)methylidene]benzenecarbo-hydrazonamide |
| 16 | | N'-[(E)-(5-methyl-2-furyl)methylidene]benzenecarbo-hydrazonamide |

-continued
| Compound No. | Formula | Name |
|---|---|---|
| 17 | 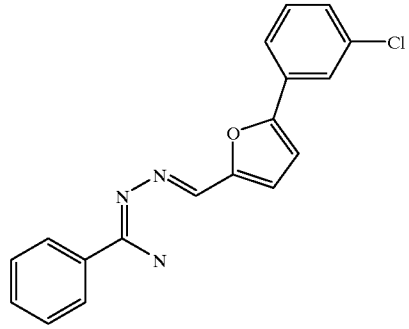 | N'-{(E)-[5-(3-chlorophenyl)-2-furyl]-methylidene}benzenecarbohydrazonamide |
| 18 | 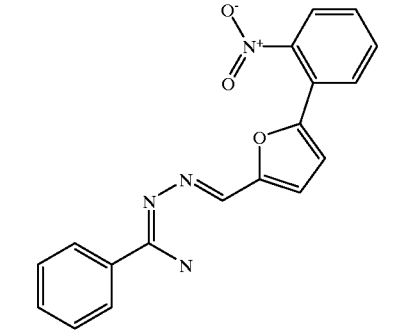 | N'-{(E)-[5-(2-nitrophenyl)-2-furyl]methylidene}benzenecarbohydrazonamide |
| 19 | 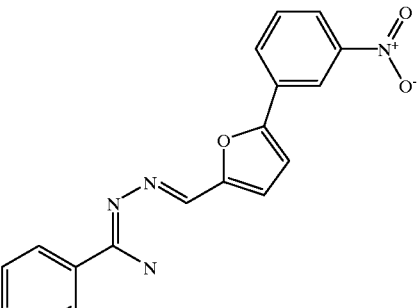 | N'-{(E)-[5-(3-nitrophenyl-2-furyl]methylidene}benzenecarbohydrazonamide |
| 20 | 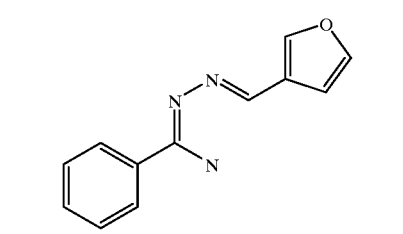 | N'-[(E)-3-furylmethylidene]benzenecarbohydrazonamide |

-continued

| Compound No. | Formula | Name |
|---|---|---|
| 21 | | [5-((E)-{(2Z)-2-[amino(phenyl)-methylene]hydrazono}methyl)-2-furyl]methyl acetate |
| 22 | | N'-{(E)-[5-(4-bromophenyl)-2-furyl]methylidine}benzencarbohydrazonamide |
| 23 | | N'-[(E)-(5-nitro-2-furyl)methylidene]benzenecarbohydrazonamide |
| 24 | | N'-[(E)-(5-ethyl-2-furyl)methylidene]benzenecarbohydrazonamide |
| 25 | | N'-[(E)-3-methylphenylmethylidene]-benzenecarbohydrazonamide |

-continued
| Compound No. | Formula | Name |
|---|---|---|
| 26 | 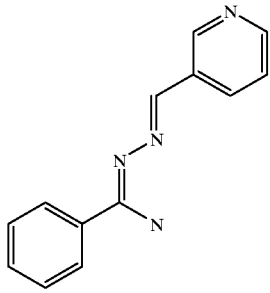 | N'-[(E)-3-pyridylmethylidene]benzene-carbohydrazonamide |
| 27 | 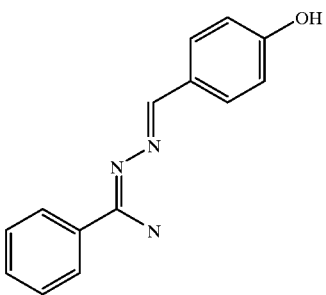 | N'-[(E)-4-hydroxyphenylmethyl-idene]benzenecarbohydrazonamide |
| 28 | 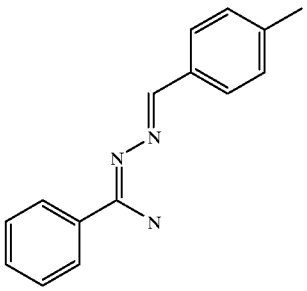 | N'-[(E)-4-methylphenylmethyl-idene]benzenecarbohydrazonamide |
| 29 | 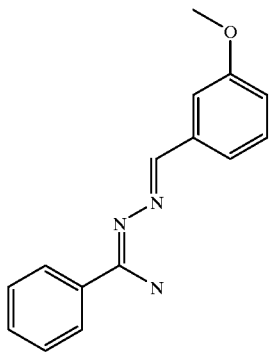 | N'-[(E)-3-methoxyphenylmethyl-idene]benzenecarbohydrazonamide |

-continued

| Compound No. | Formula | Name |
|---|---|---|
| 30 | | N'-[(E)-4-nitrophenylmethylidene]-benzenecarbohydrazonamide |
| 31 | | 5-((E)-{(2Z)-2-[amino(4-hydroxyphenyl)-methylene]hydrazono}methyl)-2-furanosulfonate |
| 32 | | N'-[(E)-1H-imidazol-2-ylmethylidene]-4-hydroxybenzencarbohydrazonamide |
| 33 | | N'-[(E)-1H-imidazol-4-ylmethylidene]-4-hydroxybenzenecarbohydrazonamide |
| 34 | | N'-[(E)-3,3-diphenyl-2-propylidene]-4-hydroxybenzenecarbohydrazonamide |
| 35 | | N'-[(E)-(5-chloro-3-methyl-1-phenyl-1H-pyrazol-4-yl)methylidene]-4-hydroxy-benzenecarbohydrazonamide |
| 36 | | N'-[(E)-(1-methyl-1H-indol-3-yl)-methylidene]-4-hydroxybenzenecarbo-hydrazonamide |

-continued

| Compound No. | Formula | Name |
|---|---|---|
| 37 | 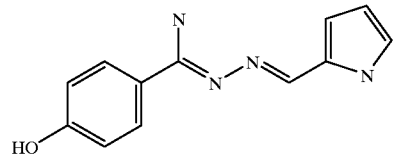 | N'-[(E)-1H-pyrrol-2-ylmethylidene]-4-hydroxybenzenecarbohydrazonamide |
| 38 | 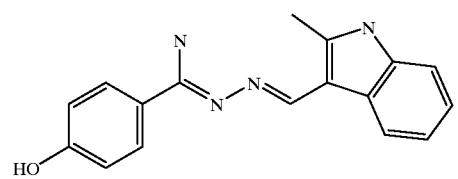 | N'-[(E)-2-methyl-1H-indol-3-yl)methylidene]-4-hydroxybenzene-carbohydrazonamide |
| 39 | 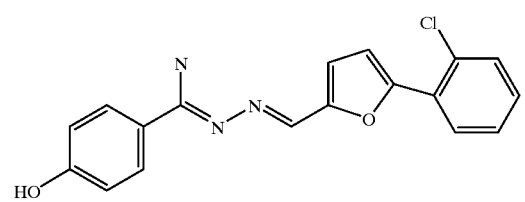 | N'-{(E)-[5-(2-chlorophenyl)-2-furyl]-methylidene}-4-hydroxybenzenecarbo-hydrazonamide |
| 40 | 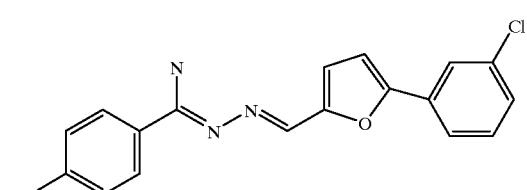 | N'-{(E)-[5-(3-chlorophenyl)-2-furyl]-methylidene}-4-hydroxybenze-carbohydrazonamide |
| 41 | 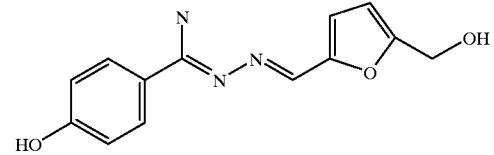 | N'-{(E)-[5-(hydroxymethyl)-2-furyl]methylidene}-4-hydroxybenzenecarbohydrazonamide |
| 42 | 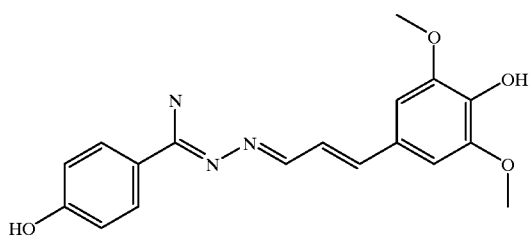 | N'-[(E,2E)-3-(4-hydroxy-3,5-dimethoxyphenyl)-2-propenylidene]-4-hydroxybenzenecarbohydrazonamide |
| 43 | 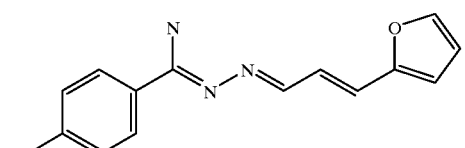 | N'-[(E,2E)-3-(2-furyl)-2-propenylidene]-4-hydroxybenzenecarbohydrazonamide |

-continued

| Compound No. | Formula | Name |
|---|---|---|
| 44 | | N'-[(E)-3-furylmethylidene]-4-hydroxybenzenecarbohydrazonamide |
| 45 | | N'-{(E)-[5-(4-nitrophenyl)-2-furyl]methylidene}-4-hydroxybenzenecarbohydrazonamide |
| 46 | | N'-[(E)-(4,5-dimethyl-2-furyl)methylidene]-4-hydroxybenzenecarbohydrazonamide |
| 47 | | N'-[(E)-(5-methyl-2-furyl)methylidene]-4-hydroxybenzenecarbohydrazonamide |
| 48 | | N'-{(E)-[5-(2-nitrophenyl)-2-furyl]methylidene}-4-hydroxybenzenecarbohydrazonamide |
| 49 | | N'-[(E)-1H-pyrrol-2-ylmethylidene]-4-hydroxybenzenecarbohydrazonamide |
| 50 | | N'-[(E)-3-furylmethylidene]-4-hydroxybenzenecarbohydrazonamide |

-continued

| Compound No. | Formula | Name |
|---|---|---|
| 51 | | 5-((E)-{(2Z)-2-[amino(2-pyrazine)-methylene]hydrazono}methyl)-2-furansulphonate |
| 52 | | N'-[(E)-2-hydroxyphenylmethyl-idene]pyrazinecarbohydrazonamide |
| 53 | | N'-[(E)-1H-imidazol-2-ylmethylidene]-2-pyrazinecarbohydrazonamide |
| 54 | | N'-[(E)-]-2-pyrazinecarbohydrazonamide |
| 55 | | N'-{(E)-[5-(hydroxymethyl)-2-furyl]-methylidene}-2-pyrazinecarbo-hydrazonamide |
| 56 | | N'-[(E)-(5-chloro-3-methyl-1-phenyl-1H-pyrazol-4-yl)methylidene]-2-pyrazine-carbohydrazonamide |
| 57 | | N'-[(E)-(1-methyl-1H-indol-3-yl)methylidene]-2-pyrazine-carbohydrazonamide |
| 58 | | N'-[(E)-1H-pyrrol-2-ylmethylidene]-2-pyrazinecarbohydrazonamide |

-continued

| Compound No. | Formula | Name |
|---|---|---|
| 59 | | N'-[(E)-(2-methyl-1H-indol-3-yl)methylidene]-2-pyrazinecarbohydrazonamide |
| 60 | | N'-[(E,2E)-3-(4-hydroxy-3,5-dimethoxyphenyl)-2-propenylidene]-2-pyraiznecarbohydrazonamide |
| 61 | | N'-[(E,2E)-3-(2-furyl)-2-propenylidene]-2-pyrazinecarbohydrazonamide |
| 62 | | N'-[(E)-2-furylmethylidene]-2-pyrazinecarbohydrazonamide |
| 63 | | N'-{(E)-[5-(2-chlorophenyl)-2-furyl]-methylidene}-2-pyrazinecarbo-hydrazonamide |
| 64 | | N'-{(E)-[5-(4-nitrophenyl)-2-furyl]methylidene}-2-pyrazinecarbohydrazonamide |
| 65 | | N'-[(E)-(4,5-dimethyl-2-furyl)methylidene]-2-pyrazinecarbohydrazonamide |

-continued

| Compound No. | Formula | Name |
|---|---|---|
| 66 | | N'-[(E)-(5-methyl-2-furyl)methylidene]-2-pyrazinecarbohydrazonamide |
| 67 | | N'-{(E)-[5-(3-chlorophenyl)-2-furyl]-methylidene}-2-pyrazine-carbohydrazonamide |
| 68 | | N'-{(E)-[5-(2-nitrophenyl)-2-furyl]methylidene}-2-pyrazinecarbohydrazonamide |
| 69 | | N'-{(E)-[5-(3-nitrophenyl)-2-furyl]methylidene}-2-pyrazine-carbohydrazonamide |
| 70 | | N'-[(E)-3-furylmethylidene]-2-pyrazinecarbohydrazonamide |
| 71 | | [5-((E)-{(2Z)-2-[amino(2-pyrazine)-methylene]hydrazono}methyl)-2-furyl]-methyl acetate |
| 72 | | N'-{(E)-[5-(4-bromophenyl)-2-furyl]methylidene}-2-pyrazine-carbohydrazonamide |

-continued

| Compound No. | Formula | Name |
|---|---|---|
| 73 | | N'-[(E)-(5-nitro-2-furyl)methylidene]-2-pyrazinecarbohydrazonamide |
| 74 | | N'-[(E)-(5-ethyl-2-furyl)methylidene]-2-pyrazinecarbohydrazonamide |
| 75 | | N'-[(E)-(5-bromo-2-furyl)methylidene]-2-pyrazinecarbohydrazonamide |
| 76 | | N'-[(E)-3-pyridinylmethylidene]-2-pyrazinecarbohydrazonamide |

The compounds of formula (I) which are more particularly preferred are:

N'-[(E)-3-methoxyphenylmethylidene]benzenecarbohydrazonamide (Compound 29);

N'-[(E)-2-hydroxyphenylmethylidene]pyrazinecarbohydrazonamide (Compound 52);

N'-[(E)-3-pyridinylmethylidene]-2-pyrazinecarbohydrazonamide (Compound 76).

Among the compounds according to the invention which are numbered from 1 to 76, most are novel and circumscribe another aspect of the invention; a few are known compounds, such as the following:

N'-[(E)-3-methoxyphenylmethylidene]benzenecarbohydrazonamide (Compound 29);

N'-[(E)-2-hydroxyphenylmethylidene]pyrazinecarbohydrazonamide (Compound 52);

N'-[(E)-1H-pyrrol-2-ylmethylidene]-2-pyrazinecarbohydrazonamide (Compound 58);

N'-[(E)-2-furylmethylidene]-2-pyrazinecarbohydrazonamide (Compound 62);

N'-[(E)-(5-methyl-2-furyl)methylidene]-2-pyrazinecarbohydrazonamide (Compound 66);

N'-[(E)-(5-nitro-2-furyl)methylidene]-2-pyrazinecarbohydrazonamide (Compound 73);

N'-[(E)-3-pyridinylmethylidene]-2-pyrazinecarbohydrazonamide (Compound 76).

In particular, compounds 29, 52 and 76 are described in the article Drug. Des. Discovery, 1998, 15(4), 269–275 and have as Registry Number (CAS.): 221084-02-2; 31649-03-3 and 221083-80-3, respectively.

The compounds of formula (I) are generally present in the compositions of the invention in proportions of from 0.1% to 20% by weight, preferably from 0.5% to 10% by weight, relative to the total weight of the composition.

The anti-sun/sunscreen cosmetic compositions according to the invention may of course contain one or more additional organic screening agents which are active in the UVA and/or UVB ranges (absorbers), and which are fat-soluble or water-soluble. These organic screening agents are advantageously selected, in particular, from among the cinnamic derivatives; dibenzoylmethane derivatives; salicylic derivatives, camphor derivatives; triazine derivatives such as those described in U.S. Pat. No. 4,367,390, EP-863,145, EP-517,104, EP-570,838, EP-796,851, EP-775,698, EP-878,469 and EP-933,376; benzophenone derivatives; β,β'-diphenylacrylate derivatives, benzimidazole derivatives; bisbenzoazolyl derivatives such as those described in EP-A-0,669,323 and U.S. Pat. No. 2,463,264; bishydroxyphenolbenzotriazol derivatives such as those described in U.S. Pat. Nos. 5,237,071 and 5,166,355, GB-A-2,303,549, DE-197,26,184 and EP-A-893,119; p-aminobenzoic acid derivatives; screening hydrocarbon polymers and screening silicones such as those described, in particular, in WO-93/04665.

Particularly exemplary additional sunscreens which are active in the UV-A and/or UV-B ranges include:
p-aminobenzoic acid,
oxyethylenated p-aminobenzoate (25 mol),
2-ethylhexyl p-dimethylaminobenzoate,
N-oxypropylenated ethyl p-aminobenzoate,
glyceryl p-aminobenzoate,
homomenthyl salicylate,
2-ethylhexyl salicylate,
triethanolamine salicylate,
4-isopropylbenzyl salicylate,
menthyl anthranilate,
2-ethylhexyl-2-cyano-3,3'-diphenylacrylate,
ethyl 2-cyano-3,3'-diphenylacrylate,
2-phenylbenzimidazole-5-sulfonic acid and salts thereof,
3-(4'-trimethylammonium)benzylidenebornan-2-one methyl sulfate,
2-hydroxy-4-methoxybenzophenone,
2-hydroxy-4-methoxybenzophenone-5-sulfonate,
2,4-dihydroxybenzophenone,
2,2',4,4'-tetrahydroxybenzophenone,
2,2'-dihydroxy-4,4'-dimethoxybenzophenone,
2-hydroxy-4-n-octoxybenzophenone,
2-hydroxy-4-methoxy-4'-methylbenzophenone,
α-(2-oxoborn-3-ylidene)-tolyl-4-sulfonic acid and salts thereof,
3-(4'-sulfo)benzylidenebornan-2-one and salts thereof,
3-(4'-methylbenzylidene)-d,1-camphor,
3-benzylidene-d,1-camphor,
1,4-benzene[di(3-methylidene-10-camphorsulfonic)] acid and salts thereof,
urocanic acid,
2,4-bis{[4-2-ethylhexyloxy)]-2-hydroxy]phenyl}-6-(4-methoxyphenyl)-1,3,5-triazine,
polymers of N-(2 and 4)-[(2-oxoborn-3-ylidene)methyl] benzyl]acrylamide,
1,4-bisbenzimidazolylphenylene-3,3',5,5'-tetrasulfonic acid and salts thereof,
polyorganosiloxanes containing a benzalmalonate functional group,
polyorganosiloxanes containing a benzotriazole functional group, such as Drometrizole Trisiloxane,
2,2'-methylenebis[6-(2H-benzotriazol-2-yl)-4-(1,1,3,3-tetramethylbutyl)phenol] in a soluble form marketed under the trademark MIXXIM BB/100 by FAIRMOUNT CHEMICAL, and in micronized insoluble form under the trademark TINOSORB M,
2,2'-methylenebis[6-(2H-benzotriazol-2-yl)-4-(methyl) phenol] marketed under the trademark MIXXIM BB/200 by FAIRMOUNT CHEMICAL.

The compositions according to the invention may also contain agents for artificially darkening and/or tanning the skin (self-tanning agents), such as, for example, dihydroxyacetone(DHA).

The compositions according to the invention may also contain pigments or nanopigments (mean primary particle size: generally ranging from 5 nm to 100 nm, preferably from 10 nm to 50 nm) of metal oxides coated or otherwise, such as, for example, nanopigments of titanium dioxide (amorphous or crystallized in the form of rutile and/or anatase state), iron oxide, zinc oxide, zirconium oxide or cerium oxide which are all UV-photoprotective agents well known per se. Conventional coating agents are moreover alumina and/or aluminum stearate. Such nanopigments of metal oxides, coated or otherwise, are, in particular, described in EP-A-0,518,772 and EP-A-0,518,773.

The compositions of the invention may comprise, in addition, conventional cosmetic additives and adjuvants, in particular selected from among fatty substances, organic solvents, thickeners, demulcents, opacifiers, stabilizers, emollients, anti-foaming agents, moisturizing agents, perfumes, preservatives, polymers, colorants, fillers, sequestrants, propellants, alkalinizing or acidifying agents or any other ingredient normally formulated into cosmetics, in particular for the production of anti-sun/sunscreen compositions in the form of emulsions.

The fatty substances may comprise an oil or a wax or mixtures thereof, and may also comprise fatty acids, fatty alcohols and fatty acid esters. The oils may be animal, vegetable, mineral or synthetic oils and, in particular, liquid petroleum jelly, paraffin oil, silicone oils, volatile or otherwise, isoparaffins, polyolefins, fluorinated and perfluorinated oils. Likewise, the waxes may be animal, fossil, vegetable, mineral or synthetic waxes known per se.

Exemplary organic solvents include the lower alcohols and polyols.

Of course, one skilled in this art will take care to select this or these possible additional compounds and/or their amounts such that the advantageous properties intrinsically associated with the aminoamidine compounds in accordance with the invention are not, or not substantially, impaired by the addition(s) envisaged.

The compositions of this invention may be formulated according to techniques well known to this art, in particular those suited for the preparation of emulsions of the oil-in-water (O/W) or water-in-oil (W/O) type.

These compositions may be provided, in particular, in the form of a simple or complex emulsion (O/W, W/O, O/W/O or W/O/W) such as a cream, a milk, a lotion, an ointment, a gel or a cream gel, of a powder or of a solid stick and may be optionally packaged as an aerosol or may be provided in the form of a foam or a spray.

When formulated as an emulsion, the aqueous phase thereof may comprise a nonionic vesicular dispersion prepared according to known techniques (BANGHAM, STANDISH AND WATKINS., *J. Mol. Biol.*, 1965, 13, 238; FR-2,315,991 and FR-2,416,008).

The cosmetic compositions of the invention are useful for protecting the human epidermis or the hair against ultraviolet radiation, as an anti-sun composition or as a makeup product.

When the cosmetic compositions according to the invention are used for protecting the human epidermis against UV radiation, or as an anti-sun composition, they may be provided in the form of a suspension or dispersion in solvents or fatty substances, in the form of a nonionic vesicular dispersion or, alternatively, in the form of an emulsion, preferably of the oil-in-water type, such as a cream or a milk, in the form of an ointment, a gel, a cream gel, a solid stick, a powder, a stick, an aerosol foam or a spray.

When the cosmetic compositions according to the invention are used for protecting the hair against UV radiation, they may be provided in the form of a shampoo, a lotion, a gel, an emulsion or a nonionic vesicular dispersion and may constitute, for example a rinse-off composition, to be applied before or after shampooing, before or after dyeing or bleaching, before, during or after permanent waving or hair straightening, a hairstyling or treatment lotion or gel, a lotion or a gel for blow-drying or hair setting or a composition for permanent waving or straightening, dyeing or bleaching the hair.

When the subject compositions are used as a makeup product for the eyelashes, the eyebrows or the skin, such as a treatment cream for the epidermis, a foundation, a lipstick, an eyeshadow, a blusher, a mascara or an eyeliner, they may be provided in solid or pasty, anhydrous or aqueous form such as oil-in-water or water-in-oil emulsions, nonionic vesicular dispersions or, alternatively, suspensions.

For example, for the anti-sun formulations in accordance with the invention which include a carrier of the oil-in-water emulsion type, the aqueous phase (comprising in particular the hydrophilic screening agents) generally constitutes from 50% to 95% by weight, preferably from 70% to 90% by weight, relative to the total weight of the formulation and the oily phase (comprising, in particular, the lipophilic screening agents) from 5% to 50% by weight, preferably from 10% to 30% by weight, relative to the total weight of the formulation.

This invention also features formulating the subject aminoamidine compounds into compositions suited for protecting materials which are sensitive to ultraviolet radiation, in particular to solar radiation.

The present invention also features formulating the subject aminoamidine compounds into cosmetic/dermatological compositions for screening out UV radiation.

Too, this invention features the use of an aminoamidine derivative of formula (I) for the production of a cosmetic composition as an agent for controlling the variation of skin color due to UV radiation.

In order to further illustrate the present invention and the advantages thereof, the following specific examples are given, it being understood that same are intended only as illustrative and in nowise limitative.

EXAMPLE 1

Preparation of N'-[(E)-(3-methoxyphenol) methylidene]benzenecarbohydrazonamide (compound 29)

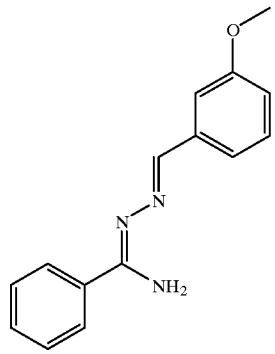

This compound was obtained according to the two-step synthesis described below from ethylbenzimidate hydrochloride (cas: 5333-86-8) and 3-methoxybenzaldehyde:

The ethylbenzimidate hydrochloride was released by the action of aqueous sodium hydroxide. The oil obtained (1 g) was dissolved in ethanol (10 ml) and then hydrazine hydrate (335 mg) was added. The reaction medium was left overnight at +4° C. and then the solvent was evaporated off, leaving the expected aminoamidine in the form of an oil. This oil was taken up in 10 ml of isopropanol and 3-methoxybenzaldehyde was added (910 mg). The medium was heated to reflux temperature and heated for 2 hours. The expected compound precipitated and was filtered.

$^1$H NMR (400 MHZ, DMSO-$d_6$, ppm): 8.43 (s, 1H); 7.97 (d, 2H) ; 7.54 (m, 1H); 7.49–7.41 (m, 4H); 7.34(t, 1H); 7.04(broad s, 2H); 6.98 (dd, 1H); 3.83(s, 3H).

$^{13}$C NMR (100 MHZ, DMSO-$d_6$, ppm):159.4; 158.7; 153; 137; 133.8; 130.2; 129.5; 128; 126.7; 121.1; 120.6; 115.7; 111.9; 55.1

Theoretical molecular mass: 237.3

Molecular mass determined from the mass spectrum of the positive ions recorded in electrospray ionization on a PLATFORM I mass spectrometer (Micromass): 238.

This compound had the following sunscreening properties:

$\lambda_{max}$=341 nm (ethanol)

spectral domain where $\epsilon$ is greater than 10,000: 297 to 377 nm.

E1% (ethanol)=1016.

EXAMPLE 2

Preparation of N'-[(E)-3-pyridinylmethylidene]-2-pyrazinecarbohydrazonamide (compound No. 76)

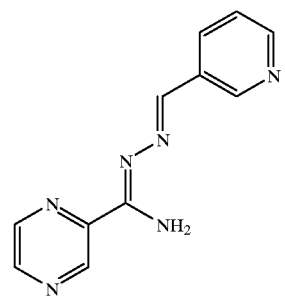

This compound was synthesized according to the procedure described by FOKS H., M. BURACZEWSKA, W. MANOWSKA, J. SAWLEWICZ, *Dissert. Pharm. Pharmacol.*, 1971, 23, (1), 49.

$^1$H NMR (400 MHZ, DMSO-$d_6$, ppm): 9.39 (d, 1H); 9.08 (d, 1H); 8.78 (d, 1H); 8.74 (d, 1H); 8.61(dd, 1H); 8.57(s, 1H); 8.38 (ddd, 1H); 7.47(m, 1H); 7.30(broad s, 2H).

$^{13}$C NMR (100 MHZ, DMSO-$d_6$, ppm): 155.7; 152.2; 150.5; 149.4; 145.9; 145.7; 143.3; 143; 134.4; 131; 123.6.

Theoretical molecular mass: 224.3

Molecular mass determined from the mass spectrum of the positive ions recorded in electrospray ionization on a PLATFORM I mass spectrometer (Micromass): 225.

This compound had the following sunscreening properties:

$\lambda_{max}$=341 nm (ethanol)

spectral domain where $\epsilon$ is greater than 10,000: 297 to 377 nm.

E1% (ethanol)=1016.

Loss of 5% after subjecting to the photostability protocol (according to BERST G., GONZPNBACH H., CHRIST R., MARTIN R., DEFLANDRE A., MASCOTTO R. E., JOLLEY J. D. R., LOWELL W., PELZER R., STIEHM T., *Inter. J. Cosm.Sci.*, 1996, 18, 167–177. Proposed protocol for determination of photostability Part I: cosmetic UV filters).

EXAMPLE 3

Preparation of N'-[(E)-2-hydroxyphenylmethylidene]pyrazinecarbohydrazonamide (compound 52)

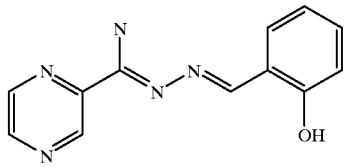

This compound was synthesized according to the following procedure:

3-cyanopyrazine (15 g) was dissolved in 30 ml of ethanol and then hydrazine hydrate (15 ml) was added. The medium was heated to reflux temperature and then the heating was stopped. The expected aminoamidine precipitated and was filtered. This aminoamidine was then used as in the procedure of Example 1.

Theoretical molecular mass: 241.3

Molecular mass determined from the mass spectrum of the positive ions recorded in electrospray ionization on a PLATFORM I mass spectrometer (Micromass): 242.

This compound had the following sunscreening properties:

$\lambda_{max}$=354.2 nm (ethanol)

spectral domain where $\epsilon$ is greater than 10,000: 320 to 384 nm.

E1% (ethanol)=1010.

EXAMPLE 4

Preparation of N'-[(E)-3-furylmethylidene]-2-pyrazinecarbohydrazonamide (compound 70)

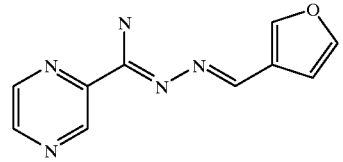

This compound was synthesized according to the procedure described by FOKS H., M. BURACZEWSKA, W. MANOWSKA, J. SAWLEWICZ, *Dissert. Pharm. Pharmacol.*, 1971, 23, (1), 49.

$^1$H NMR (500 MHZ, DMSO-$d_6$, ppm): 9.36 (d, 1H); 8.76 (dd, 1H); 8.71 (dd, 1H); 8.44(s, 1H); 8.13(broad s, 1H); 7.75 (broad s, 1H); 7.06(m, 1H); 7.02(broad s, 2H).

Theoretical molecular mass: 215.2

Molecular mass determined from the mass spectrum of the positive ions recorded in electrospray ionization on a PLATFORM I mass spectrometer (Micromass): 216.

This compound had the following sunscreening properties:

$\lambda_{max}$=335 nm (ethanol)

spectral domain where $\epsilon$ is greater than 10,000: 297 to 364 nm.

E1% (ethanol)=832.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable sunscreen/cosmetic composition suited for the photoprotection of human skin and/or hair, comprising an effective UV-photoprotecting amount of at least one aminoamidine compound, formulated into a topically applicable, cosmetically acceptable vehicle, diluent or carrier therefor.

2. The sunscreen/cosmetic composition as defined by claim 1, said at least one aminoamidine compound having the structural formula (I):

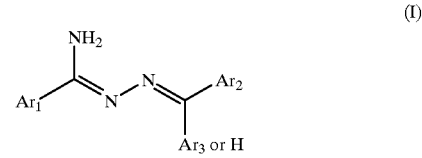

(I)

in which $Ar_1$ is (i) an aromatic radical having the following formula (II):

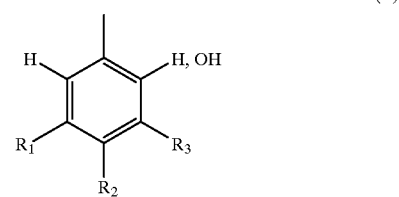

(II)

where $R_1$, $R_2$, $R_3$, which are identical or different, are each a hydrogen atom, a linear or branched $C_1$–$C_8$ alkyl radical, or a $C_1$–$C_8$ alkoxy radical, with the proviso that $R_1$, $R_2$, $R_3$ can together form an aromatic or unfused ring, or an aromatic heterocycle containing 5 or 6 atoms; or (ii) an aromatic radical having 6 atoms, corresponding to the following formula (III):

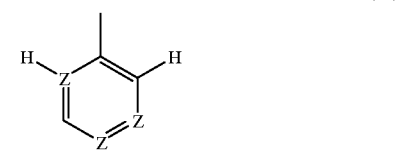

(III)

wherein each Z is C or N; $Ar_2$ is an aromatic radical $Ar_1$ as defined above or an somatic radical having 5 atoms, corresponding to the following formula (IV):

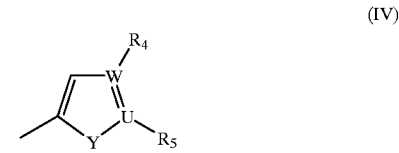

(IV)

wherein Y is a sulfur, oxygen, carbon or nitrogen atom, W is a carbon or nitrogen atom, $R_4$ is (a) a hydrogen atom when W is a nitrogen atom, or (b) a hydrogen atom, a linear or branched $C_1$–$C_8$ alkyl radical, a $C_1$–$C_8$ alkoxy radical, or can form an aromatic or unfused ring member, when W is a carbon atom; U is a carbon or nitrogen atom, when W is a carbon atom; and $R_5$ is (a) a hydrogen atom when U is nitrogen, or (b) a hydrogen atom, a linear or branched $C_1$–$C_8$ alkyl radical, a $C_1$–$C_8$ alkoxy radical, or can form an aromatic or unfused ring member, when U is a carbon atom; and $Ar_3$ is an aromatic radical $Ar_2$ as defined above, or a hydrogen atom.

3. The sunscreen/cosmetic composition as defined by claim 1, said at least one aminoamidine compound being selected from the group of Compounds Nos. 1–76 set forth in the following Table:

| Compound No. | Formula | Name |
|---|---|---|
| 1 | | 5-((E)-{(2Z)-2-amino-(phenyl)methylenehydrazono}methyl)-2-furansulfonate |
| 2 | | N'-[(E)-1H-imidazol-2-yl-methylidene]benzenecarbohydrazonamide |
| 3 | | N'-[(E)-1H-imidazol-4-yl-methylidene]benzenecarbohyrazonamide |
| 4 | | N'-[(E)-3,3-bisphenyl-2-propylidene]benzenecarbohydrazonamide |

-continued

| Compound No. | Formula | Name |
|---|---|---|
| 5 | | N'-{(E)-[5-(hydroxymethyl)-2-furyl]methylidene}benzenecarbohydrazonamide |
| 6 | | N'-[(E)-(5-chloro-3-methyl-1-phenyl-1H-pyrazol-4-yl)methylidene]benzenecarbohydrazonamide |
| 7 | | N'-[(E)-(1-methyl-1H-indol-3-yl)methylidene]benzenecarbohydrazonamide |
| 8 | | N'-[(E)-1H-pyrrol-2-yl-methylidene]benzenecarbohydrazonamide |
| 9 | | N'-[(E)-(2-methyl-1H-indol-3-yl)methylidene]benzenecarbohydrazonamide |

-continued

| Compound No. | Formula | Name |
|---|---|---|
| 10 | | N'-[(E,2E)-3-(4-hydroxy-3,5-dimethoxyphenyl)-2-propenylidene]benzenecarbohydrazonamide |
| 11 | | N'-[(E,2E)-3-(2-furyl)-2-propenylidene]benzenecarbohydrazonamide |
| 12 | | N'-[(E)-[2-furylmethylidene]benzenecarbohydrazonamide |
| 13 | | N'-{(E)-[5-(2-chlorophenyl)-2-furyl]methylidene}benzenecarbohydrazonamide |
| 14 | | N'-{(E)-[5-(4-nitrophenyl)-2-furyl]methylidene}benzenecarbohydrazonamide |

| Compound No. | Formula | Name |
|---|---|---|
| 15 | | N'-[(E)-(4,5-dimethyl-2-furyl)methylidene]benzenecarbohydrazonamide |
| 16 | | N'-[(E)-(5-methyl-2-furyl)methylidene]benzenecarbohydrazonamide |
| 17 | | N'-{(E)-[5-(3-chlorophenyl)-2-furyl]methylidene}benzenecarbohydrazonamide |
| 18 | | N'-{(E)-[5-(2-nitrophenyl)-2-furyl]methylidene}benzenecarbohydrazonamide |

-continued

| Compound No. | Formula | Name |
|---|---|---|
| 19 | | N'-{(E)-[5-(3-nitrophenyl-2-furyl]methylidene}benzenecarbohydrazonamide |
| 20 | | N'-[(E)-3-furylmethylidene]benzenecarbohydrazonamide |
| 21 | | [5-((E)-{(2Z)-2-[amino(phenyl)-methylene]hydrazono}methyl)-2-furyl]methyl acetate |
| 22 | | N'-{(E)-[5-(4-bromophenyl)-2-furyl]methylidine}benzencarbohydrazonamide |
| 23 | | N'-[(E)-(5-nitro-2-furyl)methylidene]benzenecarbohydrazonamide |

-continued

| Compound No. | Formula | Name |
|---|---|---|
| 24 | | N'-[(E)-(5-ethyl-2-furyl)methylidene]benzenecarbohydrazonamide |
| 25 | | N'-[(E)-3-methylphenylmethylidene]benzenecarbohydrazonamide |
| 26 | | N'-[(E)-3-pyridylmethylidene]benzenecarbohydrazonamide |
| 27 | | N'-[(E)-4-hydroxyphenylmethylidene]benzenecarbohydrazonamide |
| 28 | | N'-[(E)-4-methylphenylmethylidene]benzenecarbohydrazonamide |

-continued

| Compound No. | Formula | Name |
|---|---|---|
| 29 | | N'-[(E)-3-methoxyphenylmethylidene]benzenecarbohydrazonamide |
| 30 | | N'-[(E)-4-nitrophenylmethylidene]benzenecarbohydrazonamide |
| 31 | | 5-((E)-{(2Z)-2-[amino(4-hydroxyphenyl)methylene]hydrazono}methyl)-2-furanosulfonate |
| 32 | | N'-[(E)-1H-imidazol-2-ylmethylidene]-4-hydroxybenzencarbohydrazonamide |
| 33 | | N'-[(E)-1H-imidazol-4-ylmethylidene]-4-hydroxybenzenecarbohydrazonamide |
| 34 | | N'-[(E)-3,3-diphenyl-2-propylidene]-4-hydroxybenzenecarbohydrazonamide |

-continued

| Compound No. | Formula | Name |
|---|---|---|
| 35 | | N'-[(E)-(5-chloro-3-methyl-1-phenyl-1H-pyrazol-4-yl)methylidene]-4-hydroxy-benzenecarbohydrazonamide |
| 36 | | N'-[(E)-(1-methyl-1H-indol-3-yl)-methylidene]-4-hydroxybenzenecarbo-hydrazonamide |
| 37 | | N'-[(E)-1H-pyrrol-2-ylmethylidene]-4-hydroxybenzenecarbohydrazonamide |
| 38 | | N'-[(E)-2-methyl-1H-indol-3-yl)methylidene]-4-hydroxybenzene-carbohydrazonamide |
| 39 | | N'-{(E)-[5-(2-chlorophenyl)-2-furyl]-methylidene}-4-hydroxybenzenecarbo-hydrazonamide |
| 40 | | N'-{(E)-[5-(3-chlorophenyl)-2-furyl]-methylidene}-4-hydroxybenzene-carbohydrazonamide |
| 41 | | N'-{(E)-[5-(hydroxymethyl)-2-furyl]methylidene}-4-hydroxybenzenecarbohydrazonamide |

-continued

| Compound No. | Formula | Name |
|---|---|---|
| 42 | | N'-[(E,2E)-3-(4-hydroxy-3,5-dimethoxyphenyl)-2-propenylidene]-4-hydroxybenzenecarbohydrazonamide |
| 43 | | N'-[(E,2E)-3-(2-furyl)-2-propenylidene]-4-hydroxybenzenecarbohydrazonamide |
| 44 | | N'-[(E)-3-furylmethylidene]-4-hydroxybenzenecarbohydrazonamide |
| 45 | | N'-{(E)-[5-(4-nitrophenyl)-2-furyl]methylidene}-4-hydroxybenzenecarbohydrazonamide |
| 46 | | N'-[(E)-(4,5-dimethyl-2-furyl)methylidene]-4-hydroxybenzenecarbohydrazonamide |
| 47 | | N'-[(E)-(5-methyl-2-furyl)methylidene]-4-hydroxybenzenecarbohydrazonamide |
| 48 | | N'-{(E)-[5-(2-nitrophenyl)-2-furyl]methylidene}-4-hydroxybenzenecarbohydrazonamide |

-continued

| Compound No. | Formula | Name |
|---|---|---|
| 49 | | N'-[(E)-1H-pyrrol-2-ylmethylidene]-4-hydroxybenzenecarbohydrazonamide |
| 50 | | N'-[(E)-3-furylmethylidene]-4-hydroxybenzenecarbohydrazonamide |
| 51 | | 5-((E)-{(2Z)-2-[amino(2-pyrazine)-methylene]hydrazono}methyl)-2-furansulphonate |
| 52 | | N'-[(E)-2-hydroxyphenylmethyl-idene]pyrazinecarbohydrazonamide |
| 53 | | N'-[(E)-1H-imidazol-2-ylmethylidene]-2-pyrazinecarbohydrazonamide |
| 54 | | N'-[(E)-]-2-pyrazinecarbohydrazonamide |
| 55 | | N'-{(E)-[5-(hydroxymethyl)-2-furyl]-methylidene}-2-pyrazinecarbohydrazonamide |

-continued

| Compound No. | Formula | Name |
|---|---|---|
| 56 | | N'-[(E)-(5-chloro-3-methyl-1-phenyl-1H-pyrazol-4-yl)methylidene]-2-pyrazine-carbohydrazonamide |
| 57 | | N'-[(E)-(1-methyl-1H-indol-3-yl)methylidene]-2-pyrazine-carbohydrazonamide |
| 58 | | N'-[(E)-1H-pyrrol-2-ylmethylidene]-2-pyrazinecarbohydrazonamide |
| 59 | | N'-[(E)-(2-methyl-1H-indol-3-yl)methylidene]-2-pyrazinecarbohydrazonamide |
| 60 | | N'-[(E,2E)-3-(4-hydroxy-3,5-dimethoxyphenyl)-2-propenylidene]-2-pyraiznecarbohydrazonamide |
| 61 | | N'-[(E,2E)-3-(2-furyl)-2-propenylidene]-2-pyrazinecarbohydrazonamide |
| 62 | | N'-[(E)-2-furylmethylidene]-2-pyrazinecarbohydrazonamide |

-continued

| Compound No. | Formula | Name |
|---|---|---|
| 63 | | N'-{(E)-[5-(2-chlorophenyl)-2-furyl]-methylidene]-2-pyrazinecarbo-hydrazonamide |
| 64 | | N'-{(E)-[5-(4-nitrophenyl)-2-furyl]methylidene]-2-pyrazinecarbohydrazonamide |
| 65 | | N'-[(E)-(4,5-dimethyl-2-furyl)methylidene]-2-pyrazinecarbohydrazonamide |
| 66 | | N'-[(E)-(5-methyl-2-furyl)methylidene]-2-pyrazinecarbohydrazonamide |
| 67 | | N'-{(E)-[5-(3-chlorophenyl)-2-furyl]-methylidene}-2-pyrazine-carbohydrazonamide |
| 68 | | N'-{(E)-[5-(2-nitrophenyl)-2-furyl]methylidene}-2-pyrazinecarbohydrazonamide |
| 69 | | N'-{(E)-[5-(3-nitrophenyl)-2-furyl]methylidene}-2-pyrazine-carbohydrazonamide |

-continued

| Compound No. | Formula | Name |
|---|---|---|
| 70 | | N'-[(E)-3-furylmethylidene]-2-pyrazinecarbohydrazonamide |
| 71 | | [5-((E)-{(2Z)-2-[amino(2-pyrazine)-methylene]hydrazono}methyl)-2-furyl]-methyl acetate |
| 72 | | N'-{(E)-[5-(4-bromophenyl)-2-furyl]methylidene}-2-pyrazine-carbohydrazonamide |
| 73 | | N'-[(E)-(5-nitro-2-furyl)methylidene]-2-pyrazinecarbohydrazonamide |
| 74 | | N'-[(E)-(5-ethyl-2-furyl)methylidene]-2-pyrazinecarbohydrazonamide |
| 75 | | N'-[(E)-(5-bromo-2-furyl)methylidene]-2-pyrazinecarbohydrazonamide |
| 76 | | N'-[(E)-3-pyridinylmethylidene]-2-pyrazinecarbohydrazonamide. |

4. The sunscreen/cosmetic composition as defined by claim 3, said at least one aminoamidine compound comprising N'-[(E)-(3-methoxyphenyl)methylidene]benzenecarbohydrazonamide (Compound 29), having the structural formula:

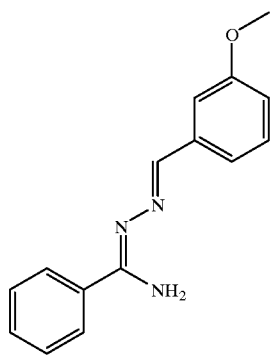

5. The sunscreen/cosmetic composition as defined by claim 3, said at least one aminoamidine compound comprising N'-[(E)-2-hydroxyphenylmethylidene]pyrazinecarbohydrazonamide (Compound 52), having the structural formula:

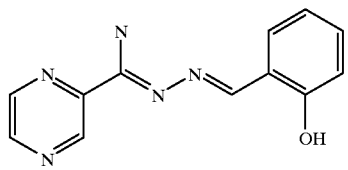

6. The sunscreen/cosmetic composition as defined by claim 3, said at least one aminoamidine compound comprising N'-[(E)-3-pyridinylmethylidene]-2-pyrazinecarbohydrazonamide (Compound 76), having the structural formula:

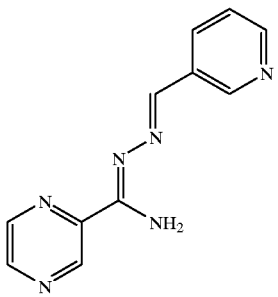

7. The sunscreen/cosmetic composition as defined by claim 2, comprising from 0.1% to 20% by weight of said at least one aminoamidine compound having the structural formula (I).

8. The sunscreen/cosmetic composition as defined by claim 7, comprising from 0.5% to 10% by weight of said at least one aminoamidine compound having the structural formula (I).

9. The sunscreen/cosmetic composition as defined by claim 2, formulated as an oil-in-water emulsion.

10. The sunscreen/cosmetic composition as defined by claim 2, further comprising at least one additional hydrophilic or lipophilic organic UV-A and/or UV-B sunscreen.

11. The sunscreen/cosmetic composition as defined by claim 10, further comprising at least one cinnamic derivative, salicylic derivative, camphor derivative, dibenzoylmethane derivative, triazine derivative, benzophenone derivative, benzimidazole derivative, bisbenzoazolyl derivative, β,β'-diphenyl-acrylate derivative, p-aminobenzoic acid derivative, sunscreen polymer, sunscreen silicone, micronized insoluble organic UV-screening agent, or mixture thereof.

12. The sunscreen/cosmetic composition as defined by claim 2, further comprising a photoprotecting effective amount of particulates of at least one coated or uncoated inorganic pigment or nonopigment.

13. The sunscreen/cosmetic composition as defined by claim 12, said at least one pigment or nanopigment comprising titanium dioxide, zinc oxide, iron oxide, zirconium oxide, cerium oxide, or mixture thereof.

14. The sunscreen/cosmetic composition as defined by claim 2, further comprising at least one active agent for the artificial tanning and/or browning of human skin.

15. The sunscreen/cosmetic composition as defined by claim 2, further comprising at least one cosmetically acceptable adjuvant or additive.

16. The sunscreen/cosmetic composition as defined by claim 2, said at least one adjuvant or additive comprising a fat, organic solvent, thickening agent, demulcent, antioxidant, opacifying agent, stabilizing agent, emollient, anti-foaming agent, hydrating agent, preservative, perfume, surfactant, sequestering agent, polymer, propellant, basifying or acidifying agent, colorant, or mixture thereof.

17. The sunscreen/cosmetic composition as defined by claim 2, comprising a nonionic vesicular dispersion, emulsion, cream, milk, gel, cream gel, ointment, lotion, suspension, dispersion, powder, solid stick or tube, foam or spray.

18. The sunscreen/cosmetic composition as defined by claim 2, comprising a make-up.

19. The sunscreen/cosmetic composition as defined by claim 18, comprising an anhydrous or aqueous solid or paste, emulsion, suspension or dispersion.

20. The sunscreen/cosmetic composition as defined by claim 2, comprising a shampoo, lotion, gel, nonionic vesicular dispersion, hair lacquer, or rinse.

21. A regime/regimen for protecting human skin and/or hair against the deleterious effect of ultraviolet irradiation, comprising topically applying thereto an effective amount of the sunscreen/cosmetic composition as defined by claim 1.

22. A regime/regimen for protecting human and/or hair against the deleterious effect of solar radiation, comprising topically applying thereto an effective amount of the sunscreen/cosmetic composition as defined by claim 1.

23. A UV-photoprotecting aminoamidine compound selected from the group consisting of the Compounds Nos. 1–28, 30–51, 53–57, 59–61, 63–65, 67–72 and 74–75 set forth in the following Table:

| Compound No. | Formula | Name |
|---|---|---|
| 1 | | 5-((E)-{(2Z)-2-amino(phenyl)methylene]-hydrazono}methyl)-2-furansulfonate |
| 2 | | N'-[(E)-1H-imidazol-2-yl-methylidene]benzenecarbohydrazonamide |
| 3 | | N'-[(E)-1H-imidazol-4-yl-methylidene]benzenecarbohyrazonamide |
| 4 | | N'-[(E)-3,3-bisphenyl-2-propylidene]benzenecarbohydrazonamide |
| 5 | | N'-{(E)-[5-(hydroxymethyl)-2-furyl]methylidene}benzenecarbo-hydrazonamide |

-continued

| Compound No. | Formula | Name |
|---|---|---|
| 6 |  | N'-[(E)-(5-chloro-3-methyl-1-phenyl-1H-pyrazol-4-yl)methylidene]benzene-carbohydrazonamide |
| 7 |  | N'-[(E)-(1-methyl-1H-indol-3-yl)methylidene]benzenecarbo-hydrazonamide |
| 8 |  | N'-[(E)-1H-pyrrol-2-yl-methylidene]benzenecarbohydrazonamide |
| 9 |  | N'-[(E)-(2-methyl-1H-indol-3-yl)methylidene]benzenecarbo-hydrazonamide |
| 10 |  | N'-[(E,2E)-3-(4-hydroxy-3,5-dimethoxyphenyl)-2-propenylidene]benzene-carbohydrazonamide |

-continued
| Compound No. | Formula | Name |
|---|---|---|
| 11 | 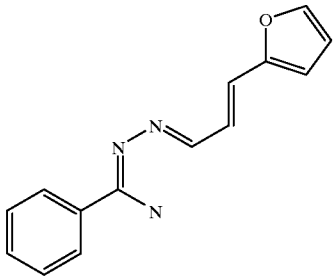 | N'-[(E,2E)-3-(2-furyl)-2-propenylidene]benzene-carbohydrazonamide |
| 12 | 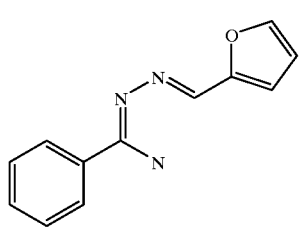 | N'-[(E)-[2-furylmethylidene]benzene-carbohydrazonamide |
| 13 | 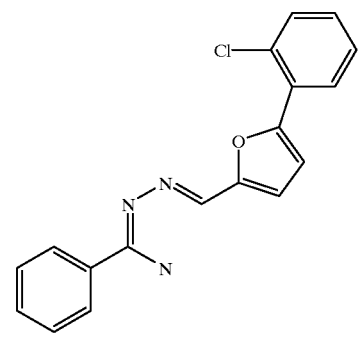 | N'-{(E)-[5-(2-chlorophenyl)-2-furyl]-methylidene}benzenecarbohydrazonamide |
| 14 | 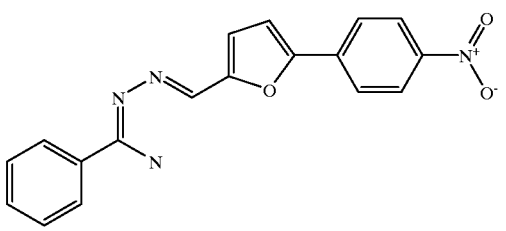 | N'-{(E)-[5-(4-nitrophenyl)-2-furyl]methylidene}benzenecarbo-hydrazonamide |
| 15 | 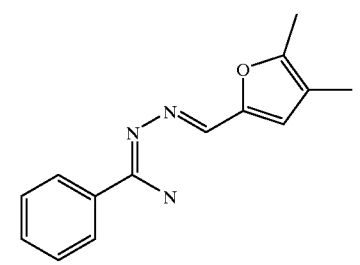 | N'-[(E)-(4,5-dimethyl-2-furyl)methylidene]benzenecarbo-hydrazonamide |

-continued

| Compound No. | Formula | Name |
|---|---|---|
| 16 | | N'-[(E)-(5-methyl-2-furyl)methylidene]benzenecarbohydrazonamide |
| 17 | | N'-{(E)-[5-(3-chlorophenyl)-2-furyl]methylidene}benzenecarbohydrazonamide |
| 18 | | N'-{(E)-[5-(2-nitrophenyl)-2-furyl]methylidene}benzenecarbohydrazonamide |
| 19 | | N'-{(E)-[5-(3-nitrophenyl-2-furyl]methylidene}benzenecarbohydrazonamide |
| 20 | | N'-[(E)-3-furylmethylidene]benzenecarbohydrazonamide |

-continued

| Compound No. | Formula | Name |
|---|---|---|
| 21 | | [5-((E)-{(2Z)-2-[amino(phenyl)-methylene]hydrazono}methyl)-2-furyl]methyl acetate |
| 22 | | N'-{(E)-[5-(4-bromophenyl)-2-furyl]methylidine}benzencarbohydrazonamide |
| 23 | | N'-[(E)-(5-nitro-2-furyl)methylidene]benzenecarbohydrazonamide |
| 24 | | N'-[(E)-(5-ethyl-2-furyl)methylidene]benzenecarbohydrazonamide |
| 25 | | N'-[(E)-3-methylphenylmethylidene]-benzenecarbohydrazonamide |

-continued
| Compound No. | Formula | Name |
|---|---|---|
| 26 | 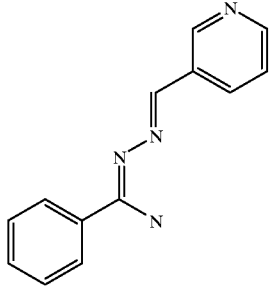 | N'-[(E)-3-pyridylmethylidene]benzene-carbohydrazonamide |
| 27 | 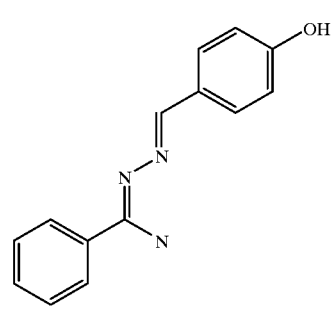 | N'-[(E)-4-hydroxyphenylmethylidene]benzenecarbohydrazonamide |
| 28 | 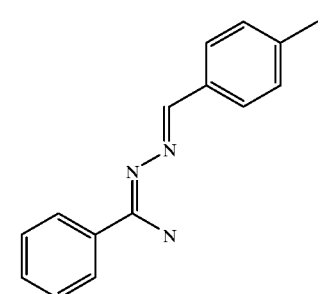 | N'-[(E)-4-methylphenylmethylidene]benzenecarbohydrazonamide |
| 30 | 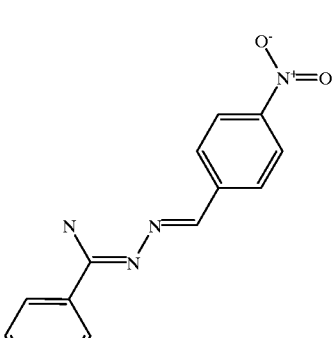 | N'-[(E)-4-nitrophenylmethylidene]-benzenecarbohydrazonamide |
| 31 | 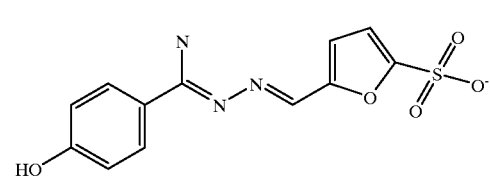 | 5-((E)-{(2Z)-2-[amino(4-hydroxyphenyl)-methylene]hydrazono}methyl)-2-furanosulfonate |

| Compound No. | Name |
|---|---|
| 32 | N'-[(E)-1H-imidazol-2-ylmethylidene]-4-hydroxybenzencarbohydrazonamide |
| 33 | N'-[(E)-1H-imidazol-4-ylmethylidene]-4-hydroxybenzenecarbohydrazonamide |
| 34 | N'-[(E)-3,3-diphenyl-2-propylidene]-4-hydroxybenzenecarbohydrazonamide |
| 35 | N'-[(E)-(5-chloro-3-methyl-1-phenyl-1H-pyrazol-4-yl)methylidene]-4-hydroxy-benzenecarbohydrazonamide |
| 36 | N'-[(E)-(1-methyl-1H-indol-3-yl)-methylidene]-4-hydroxybenzenecarbohydrazonamide |
| 37 | N'-[(E)-1H-pyrrol-2-ylmethylidene]-4-hydroxybenzenecarbohydrazonamide |
| 38 | N'-[(E)-2-methyl-1H-indol-3-yl)methylidene]-4-hydroxybenzenecarbohydrazonamide |

| Compound No. | Formula | Name |
|---|---|---|
| 39 | | N'-{(E)-[5-(2-chlorophenyl)-2-furyl]-methylidene}-4-hydroxybenzenecarbohydrazonamide |
| 40 | | N'-{(E)-[5-(3-chlorophenyl)-2-furyl]-methylidene}-4-hydroxybenzecarbohydrazonamide |
| 41 | | N'-{(E)-[5-(hydroxymethyl)-2-furyl]methylidene}-4-hydroxybenzenecarbohydrazonamide |
| 42 | | N'-[(E,2E)-3-(4-hydroxy-3,5-dimethoxyphenyl)-2-propenylidene]-4-hydroxybenzenecarbohydrazonamide |
| 43 | | N'-[(E,2E)-3-(2-furyl)-2-propenylidene]-4-hydroxybenzenecarbohydrazonamide |
| 44 | | N'-[(E)-3-furylmethylidene]-4-hydroxybenzenecarbohydrazonamide |
| 45 | | N'-{(E)-[5-(4-nitrophenyl)-2-furyl]methylidene}-4-hydroxybenzenecarbohydrazonamide |

| Compound No. | Formula | Name |
|---|---|---|
| 46 | | N'-[(E)-(4,5-dimethyl-2-furyl)methylidene]-4-hydroxybenzenecarbohydrazonamide |
| 47 | | N'-[(E)-(5-methyl-2-furyl)methylidene]-4-hydroxybenzenecarbohydrazonamide |
| 48 | | N'-{(E)-[5-(2-nitrophenyl)-2-furyl]methylidene}-4-hydroxybenzene-carbohydrazonamide |
| 49 | | N'-[(E)-1H-pyrrol-2-ylmethylidene]-4-hydroxybenzenecarbohydrazonamide |
| 50 | | N'-[(E)-3-furylmethylidene]-4-hydroxybenzenecarbohydrazonamide |
| 51 | | 5-((E)-{(2Z)-2-[amino(2-pyrazine)-methylene]hydrazono}methyl)-2-furansulphonate |
| 53 | | N'-[(E)-1H-imidazol-2-ylmethylidene]-2-pyrazinecarbohydrazonamide |

-continued

| Compound No. | Formula | Name |
|---|---|---|
| 54 | | N'-[(E)-]-2-pyrazinecarbohydrazonamide |
| 55 | | N'-{(E)-[5-(hydroxymethyl)-2-furyl]-methylidene}-2-pyrazinecarbohydrazonamide |
| 56 | | N'-[(E)-(5-chloro-3-methyl-1-phenyl-1H-pyrazol-4-yl)methylidene]-2-pyrazinecarbohydrazonamide |
| 57 | | N'-[(E)-(1-methyl-1H-indol-3-yl)methylidene]-2-pyrazinecarbohydrazonamide |
| 59 | | N'-[(E)-(2-methyl-1H-indol-3-yl)methylidene]-2-pyrazinecarbohydrazonamide |
| 60 | | N'-[(E,2E)-3-(4-hydroxy-3,5-dimethoxyphenyl)-2-propenylidene]-2-pyraiznecarbohydrazonamide |
| 61 | | N'-[(E,2E)-3-(2-furyl)-2-propenylidene]-2-pyrazinecarbohydrazonamide |

-continued

| Compound No. | Formula | Name |
|---|---|---|
| 63 | | N'-{(E)-[5-(2-chlorophenyl)-2-furyl]-methylidene]-2-pyrazinecarbo-hydrazonamide |
| 64 | | N'-{(E)-[5-(4-nitrophenyl)-2-furyl]methylidene]-2-pyrazinecarbohydrazonamide |
| 65 | | N'-[(E)-(4,5-dimethyl-2-furyl)methylidene]-2-pyrazinecarbohydrazonamide |
| 67 | | N'-{(E)-[5-(3-chlorophenyl)-2-furyl]-methylidene}-2-pyrazine-carbohydrazonamide |
| 68 | | N'-{(E)-[5-(2-nitrophenyl)-2-furyl]methylidene}-2-pyrazinecarbohydrazonamide |
| 69 | | N'-{(E)-[5-(3-nitrophenyl)-2-furyl]methylidene}-2-pyrazine-carbohydrazonamide |
| 70 | | N'-[(E)-3-furylmethylidene]-2-pyrazinecarbohydrazonamide |

-continued
| Compound No. | Formula | Name |
|---|---|---|
| 71 | 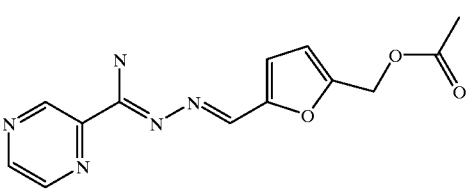 | [5-((E)-{(2Z)-2-[amino(2-pyrazine)-methylene]hydrazono}methyl)-2-furyl]-methyl acetate |
| 72 | 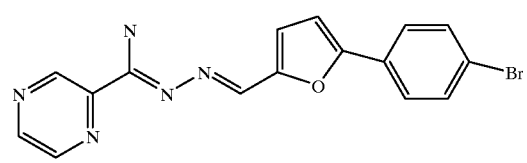 | N'-{(E)-[5-(4-bromophenyl)-2-furyl]methylidene]-2-pyrazine-carbohydrazonamide |
| 74 | 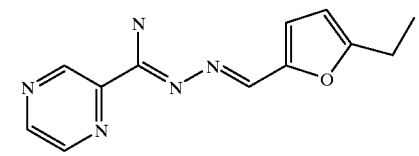 | N'-[(E)-(5-ethyl-2-furyl)methylidene]-2-pyrazinecarbohydrazonamide |
| 75 | 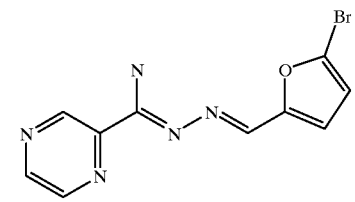 | N'-[(E)-(5-bromo-2-furyl)methylidene]-2-pyrazinecarbohydrazonamide. |
\* \* \* \* \*